United States Patent [19]

Pollock et al.

[11] Patent Number: 4,861,582
[45] Date of Patent: * Aug. 29, 1989

[54] DENTAL COMPOSITIONS CONTAINING MONOVALENT IONS

[75] Inventors: Jerry J. Pollock, Nesconset; Thomas F. McNamara, Port Jefferson, both of N.Y.

[73] Assignee: The Research Foundation of State University of New York, Albany, N.Y.

[*] Notice: The portion of the term of this patent subsequent to Oct. 21, 2003 has been disclaimed.

[21] Appl. No.: 886,276

[22] Filed: Jul. 16, 1986

[51] Int. Cl.$^4$ .......................... A61K 9/16; A61K 9/18
[52] U.S. Cl. ...................... 424/520; 424/49; 424/48; 424/464; 424/611; 424/676; 424/717; 514/901
[58] Field of Search ....................... 424/49, 52, 43, 48, 424/50, 94, 151, 153, 129; 514/835, 901

[56] References Cited

U.S. PATENT DOCUMENTS

| | | | |
|---|---|---|---|
| 3,119,743 | 1/1964 | Ericsson | 424/52 |
| 3,867,557 | 2/1975 | Neely | 424/52 |
| 3,937,804 | 2/1976 | Delaney et al. | 424/52 |
| 3,975,514 | 8/1976 | Weisz | 424/52 |
| 4,024,237 | 5/1977 | Eichel | 424/49 |
| 4,083,955 | 4/1978 | Grbenstetter | 424/49 |
| 4,150,151 | 4/1917 | Pader et al. | 424/56 |
| 4,370,314 | 1/1983 | Gaffar | 424/54 |
| 4,575,457 | 3/1986 | Mazarin | 424/52 |
| 4,618,489 | 10/1986 | Pollock | 424/49 |

OTHER PUBLICATIONS

Acta Odortologica Scand. 17, 131 (1959).
American Scientist, 67, 680-688 (1974).
Infection and Immunity, pp. 1-6 (1984), vol. 46.
Infection and Immunity, vol. 46, No. 3, pp. 765-772, (1984).
Infection and Immunity, vol. 38, No. 3, pp. 1137-1148n (1982).
Infection and Immunity, vol. 42, No. 2, pp. 510-515 (1983).
Science, vol. 217, pp. 26∝30 (1982).
Europ. J. Clin. Invest. 2, 393-406 (1972).
Archs Oral Biol. 14, pp. 277-294, Pergamon Press (1969).
Information Retrieval, Inc., Microbial Aspects of Dental Caries, pp. 869-886.
Archs Oral Biol. 21, pp. 313-317, Pergamon Press (1976).
Caries Res. 4, pp. 332-346 (1970).
Cariology Today, Int. Congr., pp. 56-69 (1983).
Saliva and Dental Caries, Sp.Supp. Microbiology Abstracts, pp. 429-448 (1979).
Infection and Immunity, 44, pp. 386-393 (1984).
Jo. of Bacteriology, 146, No. 2, pp. 764-774 (1981).
Infection and Immunity, 45, pp. 610-617 (1984).
Infection and Immunity, 44, pp. 702-707 (1984).
Archs Oral Biol. 28, pp. 865-871 (1983).
Infection and Immunity, 38, No. 3, pp. 1172-1180 (1982).
Scand.J.Dent.Res. 87, pp. 197-207 (1979).
Archs Oral Biol. 26, pp. 711-716 (1981).
The Physiology and Biochemistry of the Mouth, Jenkins, SALIVA, pp. 284-359.
Medical Progress, Microbial Synergism in Human Infections, (1978).
Cummunity Dent. Oral Epidemiol, 10, 124-129 (1982).
Caries Research, 17, 139-144 (1983).
Caries Research, vol. II, Supplement (1977), Cariostatic Mechanisms of Fluorides.
Gershon in Cosmetics: *Science and Technology*, 2nd ed., edited by Sagarin et al., Wiley-Intersciences, pp. 424-439, 1972.
*Federal Register*, vol. 45, No. 62, Mar. 28, 1980, pp. 20669-20670, *Classification of Ingredients*.
*Remingtons Pharmaceutical Sciences*, 16th ed., Osal editor, Mack Publishing Co., Easton Pa., 1980, pp. 1892-1893.
Pollock et al., *Infection and Immunity*, vol. 45, No. 3, 610-617 (1984).

*Primary Examiner*—Howard E. Schain
*Assistant Examiner*—F. T. Moezie
*Attorney, Agent, or Firm*—Omri M. Behr

[57] ABSTRACT

Dental compositions containing bicarbonate anion in combination with a monovalent anion such as fluoride, chloride or thiocyanate and methods of using them in anti-carogenic, antiplaque and antiperiodontopathic therapy are disclosed herein.

3 Claims, 9 Drawing Sheets

DENTAL COMPOSITIONS CONTAINING MONOVALENT IONS

"This invention was made with Government support under the National Institute of Dental Research awarded by contract DE 04296. The Government has certain rights in the invention".

RELATED APPLICATIONS

This application is a continuation-in-part of Applicants' copending application, Ser. No. 529,163, filed Sept. 2, 1983, now U.S. Pat. No. 4,618,489.

BACKGROUND OF THE INVENTION

Microorganisms, either singly or as a group, are generally accepted to be the primary etiological agents responsible for the initiation of dental caries, periodontal disease, and dental infections. In the healthy mouth, the number of microorganisms may not reach the threshold level required to initiate oral disease (the threshold may be different both for different micoorganisms in a given flora and for different individuals), in large part because of the regulation by the immunoglobulins and by a series of proteins commonly described as the non-immune host defense factors (for example, lysozyme, lactoperoxidase, lactoferrin, histidine-rich polypeptides) (Mandel, "Microbial Aspects of Dental Caries", 3, pp. 589-866, 1976; Mandel, Amer. Sci., 67, pp. 680-688, 1979; Pollock, et al., Infect. Immun. 44, pp. 702-707, 1984). However, when the delicate belance between host and pathogen is tipped in favor of the microbes, human infection can result in the susceptible host (Mackowiak, New Eng. J. Med., 298, pp. 21-26 and 83-87, 1978).

In the oral cavity, a number of microbial species make up the dental plaque; however, only some of these microbes become pathogenic and initiate dental caries and periodontal disease when their numbers rise above the threshold level for disease. In the case of dental enamel (cavities of the smooth and interproximal areas of the teeth) and fissure (cavities of molar teeth) caries in both children and adults, the pathogenic organisms have been fairly conclusively shown to be specific immunological serotypes of *Streptococcus mutans* and various species of Lactobacilli (Loesche, et al., Infect. Immun., 46, pp. 765-772, 1984). Both *S. mutans* and the Lactobacilli are the most acidogenic (highest production of acid) and aciduric (able to survive at low acid pHs of 4 to 5.5 with continued production of acid) microbial species in the dental plaque. In the case of adult root caries (cavities located in exposed areas of dentin on the roots of the teeth), pathogenic species have not been conclusively identified; however, Actinomyces species have been suggested since they do produce sufficient acid for dissolving the dentin (usually at pHs of 5.5 or greater) and more importantly are one of the major members of the supragingival (where the gum margin meets the tooth surface) bacterial floras (Moore, et al., Infect. Immun., 46, pp. 1-6, 1984). In the case of gingivitis or mild periodontal disease which, in turn, can lead to more advanced disease, Actinomyces species such as *A. viscosus* and *A. naeslundii* may be causative agents as may be *Fusobacterium nucleatum* (Moore, et al., Infect. Immun., 46, pp. 1-6, 1984; Moore, et al., Infect. Immun., 42, pp. 510-515, 1983). In more advanced severe periodontal disease, *Fusobacterium nucleatum* has been suggested to be the major pathogen of the subgingival flora (DiRienzo and Rosan, Infect. Immunity, 44, pp. 386-393, 1984; Moore et al., Infect. Immun., 38, pp. 1137-1148, 1982).

There are a number of approaches to the treatment of dental caries which is known to be multifactorial in nature. For example, it is well documented that limiting the amount of ingested sugar and thus the amount of acid produced can reduced the incidence of cavities. Unfortunately, such self-limitation in most population groups usually remains modest and is easily reversible. For this reason, caries preventive and treatment measures such as (i) mechanical debridement of the teeth with toothpastes or rinses, etc., to remove bacterial plaque, (ii) remineralizing and enamel fortifying solutions, (iii) over-the-counter dental products containing plaque adherence inhibitors, (iv) dental products containing agents which raise/or maintain the pH of the saliva or dental plaque, and (v) over-the-counter dental products containing antibacterials have all come into use. To date, the most important caries preventive measure is fluoride in the form of fluoridated water, fluoridated toothpastes and rinses, and fluoridated-supplemented vitamins and foodstuffs. Fluoride is thought to act by fortifying the enamel, by maintaining the pH and by serving as an antibacterial agent (Brown and Konig, "Cariostatic Mechanisms of Fluoride", pp. 1-327, 1977), but under normal treatment it reduces cavities only to the extent of about 25 to 30%. Long-term disciplined supplementation of fluoride in the form of fluoride rinses has resulted in caries reduction of greater than 50% in school children (Leverett, Science, 217, pp. 26-30. 1982). However, in the public view, there is a rising concern over the possibility of fluoride toxicity because of the need for continuous daily rinsing at reasonably high fluoride concentrations.

To date, the antibacterial agents (including fluoride) used for the treatment of dental caries rely on either a bacteriostatic (growth inhibition) or bactericidal (inhibition of the multiplication of the bacteria) activity. Most of these agents therefore suffer from the fact that the bacteria can both reverse these effects and can still metabolize sugars to produce acid which in turn can destroy the teeth. It would be desirable to overcome these disadvantages in achieving as the antibacterial effect, bacterial cell lysis. Under bacteriolytic conditions, the cariogenic pathogens are destroyed irreversibly and no acid can therefore be produced.

Bicarbonate, fluoride, chloride and thiocyanate are the major monovalent anions normally present in human saliva (Pollock, et al., Archs. Oral. Biol. 26, 711-716, 1981). The concentrations of each of these anions have been observed to vary with salivary flow rate and with duration of collection at fixed flow rates (Dawes Archs., Oral. Biol., 14, pp. 277-294, 1969; Jenkins, "The Physiology and Biochemistry of the Mouth", 4th. Edition, pp. 284-359, 1978; Kreusser, et al., Eur. J. Clin. Invest., 2, pp. 398-406, 1972). Natural, normal physiologic concentrations in submandibular, parotid and mixed human salivas range for bicarbonate from 1 to 60 millimolar, for chloride from 10 to 50 millimolar and thiocyanate from 0.5 to 4.5 millimolar (Jenkins, supra.). After a mouth rinse for two minutes with 0.2% sodium fluoride, salivary fluoride concentrations were found to average 36 millimolar (Brunn, et al., Community Dent. Oral Epidemiol., 10, pp. 124-129, 1982). At neutral pH (or at pHs at least greater than 6.0), all four anions (when supplied as inorganic salts) will activate cell lysis (Pollock, et al., Archs Oral Biol., 26, 711–716, 1981; Wilkens, et al., Infect. Immun., 38, 1172–1180, 1982) but at acidic pHs of 5 or 4 (corresponding to the pHs of the carious lesion) only bicarbonate when used alone will cause the cariogenic pathogens to lyse (Pollock, et al., Archs. Oral. Biol., 28, 865–871, 1983; Pollock, et al., Infect. Immun., 45, 610–617, 1984). In the human mouth, the amount of bicarbonate secreted by a individual has been proposed to be of critical importance to dental caries. We propose that this is not so much due to the buffering capacity of the bicarbonate anion as suggested by other investigators (Agus and Schamschula, Caries Res., 17, 139–144, 1983; Pickerill, "The Prevention of Dental Caries and Oral Sepsis", 1912; Hubbell, Am. J. Physiol., 105, pp. 436–442, 1933; Ericsson, Acta Odont. Scand., 11, pp. 179–194, 1954) but rather to the ability of bicarbonate to activate bacteriolysis of lysozyme-protease damaged microbes as suggested originally by us (Pollock, et al., Archs. Oral Biol., 26, 711–716, 1981; Goodman, et al., J. Bacteriol., 146, 764–774, 1981). It should be pointed out that the inorganic salts of divalent anions such as carbonate or phosphate, will not activate cell lysis for biochemical reasons discussed in our publications (Pollock, et al., "Saliva and Dental Caries", pp. 429–447, 1979; Goodman, et al., J. Bacteriol., 146, 764–774 (1981).

Heretofore, use of combinations of these inorganic monovalent anions (preferably as their sodium salts) for the lysis of oral pathogens, particularly those like *S. mutans* and Lactobacilli with known cariogenic potential has not been proposed. Although these salts have been combined together in previous formulations, in many instances these combinations are only incidental to the formulations proposed. For example, Delany, et al., (Patent 3,937,804) use fluoride as their anti-caries agent but make no anti-caries claims for bicarbonate which is used at very high salt concentrations to give the consumer a clean mouth. Or for example, Pader, et al. (Patent 4,150,151) uses sodium chloride as an electrolyte and flavoring agent while proposing an anionic surfactant mouthwash which may include fluoride. In both of these examples, no claim is made for the combination of these inorganic salts as lytic agents for the elimination of pathogenic organisms associated with dental caries (and periodontal disease). In one patent by Weisz (3,975,514), a fluoride mouthwash composition was proposed in which both chloride and an anionic surface active wetting agent were minor components. It was stated that the ionic surface active agent plus the sodium chloride provided an enhancing antibacterial potential of the fluoride.

Clinical studies have shown that marked caries reduction can be obtained by bicarbonate-phosphate or bicarbonate-phosphate-fluoride combinations mixed into the dietary sugar of rats (Luoma, et al., Caries Res., 4, pp. 332–346, 1970). These studies have been followed by experiments in a controlled population of institutionalized mentally handicapped children. The results have shown that the inclusion of fluoride and a bicarbonate-phosphate mixture in sweet sugar products of the children's diet produces caries arrestment after the first year (Luoma, et al., Scand. J. Dent. Res., 87, pp. 197–207, 1979). In these studies, Luoma added the bicarbonate fraction mainly to serve as the buffering agent while the phosphate component (a divalent anion) was added to satisfy the phosphate need of cariogenic bacteria in order to prevent the enamel phosphate from being utilized for the bacteria's metabolic need. Again, lysis of bacteria by the combination of fluoride and bicarbonate was not discussed so that clinical studies did not include a therapeutic anti-caries design based on an optimal lysis concentration range of these anions.

SUMMARY OF THE INVENTION

The present invention relates to compositions adapted for anticariogenic, antiplaque and antiperiodontopathic therapy. These compositions comprise bicarbonate anion and provide an "in mouth" concentration of 10–120 millimolar bicarbonate anion. They further comprise chloride and/or thiocyanate ion and, if desired fluoride ion to provide "in mouth" concentrations of 20–100 millimolar of said monovalent anion, or mixtures thereof.

The compositions are administered in a vehicle suitable for oral or oral cavity administration, said composition being substantially free of divalent anions. This invention also relates to a method of using such compositions for treating and inhibiting dental caries, plaque and periodontopathic conditions in mammals, particularly humans, in need of anti-caries, antiplaque or antiperiodontopathic therapy.

In particular, the invention comprises enhancing the ability of enzymes such lysozyme, trypsin and (as they usually are found in the oral cavity) to lyse gram positive cariogenic bacteria, such as *Streptococcus mutans, Lactobacillus casei, Lactobacillus plantarum, Actinomyces viscous* and *Actinomyces naeslundii*. This list of lysable bacteria is not considered exhaustive, merely illustrative.

The lysis of the gram negative bacterium *Veillonella alcalescens* and the gram-negative periodontopathogen *Fusobacterium nucleatum* has also been observed using compositions of the present invention.

The anion can be formulated in the composition in the form of its potassium, sodium, calcium and other non-toxic, pharmacologically acceptable salt. Particularly preferred for purposes of this invention is the sodium salt of the monovalent anion.

The bicarbonate anion utilized in the compositions of the present invention can likewise be utilized in the form of potassium, sodium, calcium or other non-toxic pharmacologically acceptable salt. For ease of formulation in the present invention, the sodium salt is preferred.

The "in mouth" concentrations of the monovalent anion delivered by the compositions of the present invention range from 20–100 millimolar, with a range of 30–60 millimolar being generally used.

The "in mouth" concentrations of bicarbonate anion delivered by the compositions of the present invention in an amount of about 10–120 millimolar with a range of about 30–80 millimolar being generally preferred.

Depending on the compositions used, the concentrations in the actual compositions will vary within a fairly wide range. Thus, the bicarbonate concentration in the compositions (expressed as either % weight by weight or % weight by volume) may range from about 0.08% to about 1%, the chloride concentration from about 0.12% to about 0.60%, the thiocyanate concentration from about 0.16% to about 0.80% and the fluoride concentration between about 0.05% to about 0.40%. More specific compositions are set forth in the Examples.

The compositions of the present invention are conventionally formulated into the commonly utilized dental treatment agents, i.e., dentrifices, mouthwashes and toothpastes, as well as into typically chewed carriers such as gum, candies and vitamins. For instance, the fluoride anion, commonly incorporated into dentifrices, mouthwashes, toothpastes and vitamins can be incorporated at similar lower levels with greater effectiveness by virtue of the present invention.

The method of utilizing the compositions of the present invention involves treatment of mammals, particularly humans, in need of anti-caries therapy with an anti-caries effective amount of the compositions of the present invention.

Obviously, the anti-caries effective amount will vary with the particular formulations utilized. Typically, the composition will be administered from one to three times daily.

While it has been found effective to enhance the enzymatic lysis of cariogenic bacteria in the situs of the oral cavity, the invention is not limited to the enhancement of the lytic process of these bacteria in that location.

In order to achieve the anti-caries effect, the compositions should consist as active agents essentially of bicarbonate, in combination with either chloride or thiocyanate or in combination with both. If desired, fluoride may also be present.

In order to achieve an antiperiodontopathic effect, or an antiplaque effect, similar compositions are effective.

The synergistic properties of the compositions of the present invention are determined by standardized assay procedures involving the bacteriolysis of *Streptococcus mutans* GS 5. The lysis is assayed by release of tritiated thymidine. The percentage of lysis is indicative of the ability of the composition to destroy the decay-causing microorganisms in the oral cavity.

The basis of the present invention, however, does not employ bicarbonate alone as a lytic agent because this anion is know to poorly penetrate human dental plaque (Tatevossian, Caries Res., 13, 154-162, 1979). Rather, we have made the unique discovery that bicarbonate, which is essential to our invention, can act synergistically to lyse pathogens when combined with one or more of fluoride, chloride or thiocyanate (as their sodium salts). With respect to cariogenic bacteria at acidic pHs, sublytic concentrations of the bicarbonate can be combined with one or more of fluoride, chloride, or thiocyanate (in themselves the latter three anions are non-lytic at the acidic pHs). As the bicarbonate concentration is raised, the synergistic bacterial lysis is increased dramatically. Therefore, an individual's ability to defend against dental caries may depend upon that person's total oral concentration of all four inorganic monovalent anions and not just bicarbonate so that if this total salt concentration is low, such individuals, we would suggest, would benefit from salt supplementation. Because our studies have shown that only slight increases in the concentration of these anions would be necessary to effect marked changes in cell lysis, our proposed formulations utilize dilute solutions of these salts either within the concentration range or just above their normal oral physiological levels. Our preparations therefore offer no toxicity problems. An added attraction of our cell lysis system is that bicarbonate operates synergistically with fluoride, the latter being presently the only Food and Drug approved anticaries agent on the commercial market. Therefore, if fluoride is used in our combined synergistic salt formulations, then lower concentrations of the fluoride would be necessary to achieve better caries reductions in comparison to preparations employing fluoride alone. In this invention, we also show that lysis of the periodontopathogen, Fusobacterium nucleatum can be achieved using our therapeutic regimen of sodium bicarbonate plus other monovalent anion salts such as sodium chloride. Again, physiological concentrations of the salts are proposed for the lysis of this pathogen.

BRIEF DESCRIPTION OF THE DRAWINGS

FIG. 1 (A-D) is a set of Bar graphs showing thymidine release (lysis) as various single anion concentrations with varying enzyme concentrations.

FIG. 6 (A & B) are Bar graphs of the lysis obtained with sublytic concentrations of bicarbonate anion and combinations with fluoride, chloride and thiocyanate.

FIG. 7 (A & D) is a series of plots of optical density (lysis of various bacteria) against incubation time for cells treated with lysozyme, trypsin and a mixture of bicarbonate/thiocyanate and chloride against lysozyme plus trypsin, but without salts.

EXAMPLES

The materials and method of the assay are as follows:

Chemicals

All chemicals are of the highest purity available. Sodium chloride (biological grade), sodium thiocyanate (ACS grade), sodium bicarbonate (ACS grade), sodium acetate and acetic acid are obtained from Fisher (Springfield, N.J.). Sodium fluoride (analytical grade) is obtained from Baker (Phillipsburg, N.J.). HEPES (N-2-hydroxyethylpiperazine-N-2-ethane sulfonic acid) (ultrol grade) and MES (2-N-morpholino) ethane sulfonic acid) are obtained from Calbiochem (La Jolla, Calif.). (Methyl-$^3$H)-thymidine is a product of ICN Pharmaceuticals (Irvine, Calif.). NCS is obtained from Amersham Corp. (Arlington Heights, Ill.) and Soluscint O from National Diagnostics (Somerville, N.J.). Hen egg white lysozyme (HEWL, 3x crystallized), trypsin (bovine pancreas, type III) and alpha chymotrypsin (Type II, 3x crystallized) are obtained from Sigma Chemical Co. (St. Louis, Mo.). The concentrations of HEWL is determined from the extinction coefficient of $E^{1\%} = 26.9$ (Kuramitsu, et al., *J. Biochem.*

1 cm (Tokyo, 78, pp.327-333 (1975)).

Bacterial Cultures

*S. mutans* GS5 is obtained from Dr. Harold Jordan (Forsyth Dental Center, Boston). Stock cultures grown to late exponential phase in brain heart infusion (BHI) broth (Difco Laboratories, Detroit, Mich.) are stored quick-frozen at $-90°$ C. in 1% skim milk. During the course of these experiments, it became necessary to freeze-down a second batch of cultures. For routine use, freshly grown cells are inoculated as either 1:100,00 or 1:100,000 dilutions in FMC synthetic media (10 ml) supplemented with NaHCO3 (0.01M final concentration) (Terleckyj, Willett and Shockman, Infect. Immun., 11, pp 649-655 (1975)) and 10 uCi/ml (methyl-$^3$H)-thymidine (sp.act. 1 mCi/ml, 20 Ci/mmole) (Pollock, et al., Archs. Oral. Biol., 26, pp. 711-716 (1981). Bacteria are harvested in the log phase of growth (optical density 0.68 at 675 nm) and washed three times in ice-cold distilled water. Cells are then resuspended in buffers of selected pH and an ionic strength of 0.025 to an optical density at 700 nm of 0.20 ($5.6 \times 10^8$ cells/ml, Petroff-Hausser bacterial chamber) immediately prior to lytic assays.

Assays

Lysis is assayed by release of tritiated thymidine from *S. mutans* GS 5 as previously described (Pollock, et al., Arch. Oral Biol., 26, pp. 711-716 (1981); Goodman, et al., J. Bacteriol., 146, pp. 764-774 (1981).

The effects of bicarbonate on lysis is determined by experiments conducted in either MES buffer, pH 5.2, or acetate buffer, pH 4.0 ($^3$H)-thymidine suspensions are first preincubated for one hour with stirring at 37° C. after which cells were treated with trypsin (75 μg/ml), lysozyme (30 μg/ml) or a combination of HEWL plus trypsin. After 2 hours incubation with the enzymes, varying concentrations of sodium bicarbonate (0.01 to 0.15M final molarity) are added, the pH immediately recorded and the cells further incubated with a bicarbonate for an additional 2 hour period. At this time, 1 ml samples are removed, blended in a Vortex mixer and processed for DNA release (Goodman et al., J. Bacteriol., 146, pp. 764-774 (1981). Aliquots of 0.1 ml are removed for total counts (MARK III Liquid Scintillation Counter, Tracor Analytic) and the remainder is centrifuged at 2,100 g for 20 min. at 4° C. Radioactivity is similarly measured in the resultant supernatants (0.1 ml) using a mixture of NCS and Soluscint O and the percentage of ($^3$H)-thymidine released is then calculated.

The effect of the four sodium salts, fluoride, chloride, thiocyanate and bicarbonate, on the bacteriolysis of *S. mutans* GS5 treated with lysozyme (30 μg or 75 μg/ml) and chymotrypsin (1 μg/ml) in 0.025M Hepes buffer, pH 7.3 is determined as follows: Cells are preincubated in the buffer with stirring at 37° C. After one hour, various concentrations of HEWL are added and incubation continued for an additional two hours. One milliliter of cell suspension is then placed into 15 ml polystyrene disposable centrifuge tubes (Falcon, Oxnard, Calif.) containing 100 μl of aqueous stock salt solutions such that the final salt molar concentrations are 0.03, 0.05, 0.07, 0.09 and 0.10M. Immediately upon mixing cells with salts, tubes are mixed vigorously with a Vortex mixer for 15 seconds and are then shaken at 300 rpm in a Psychrotherm G26 LIncubator (New Brunswick Scientific, New Brunswick, N.J.). During the subsequent 2 hours, tubes are intermittently mixed with a Vortex mixer. At the end of the reaction period, samples are quantitated for release of ($^3$H)-thymidine as described above.

Varying concentrations of fluoride, chloride or thiocyanate (0.01 to 0.1M final molarity) are combined with fixed concentrations of bicarbonate and added to reaction mixtures containing 30 μg HEWL/ml and 1 μg trypsin/ml in MES buffer, pH 5.2. Additional experiments are carried out at the lower pH the same conditions using either two or all three of the sodium salts in combination with bicarbonate, trypsin and HEWL. Lysis is quantitated as described above.

ASSAY RESULTS

Comparison of Effectiveness of

Inorganic Anions in Cell Lysis at Neutral pH

Figure 1A:
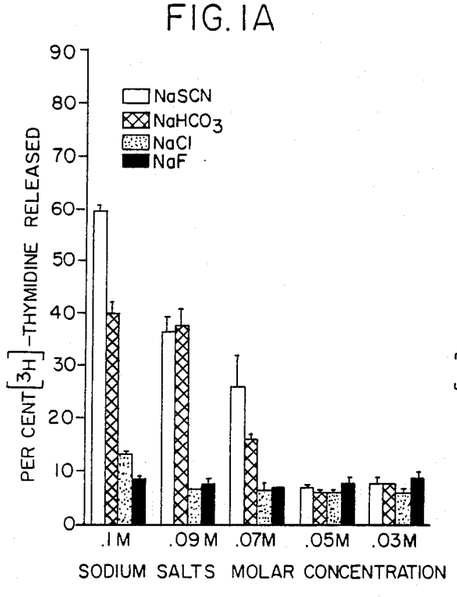
Figure 1B:
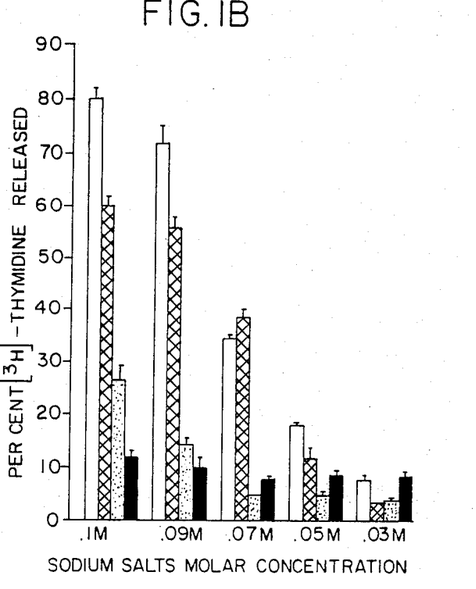
Figure 1C:
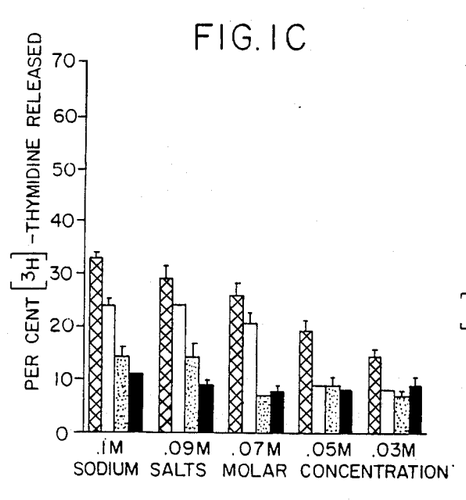

Lytic effectiveness is monitored at neutral pH at two HEWL concentrations with or without chymotrypsin. With HEWL alone, only the sodium salts of $HCO_3^-$ and $SCN^-$ are effective in promoting cell lysis as NaF and NaCl caused the release of less than 15% of radiolabeled thymidine which has previously been determined to be mainly pool thymidine or small molecular weight thymidine nucleotides (Goodman, et al., 1981; Pollock, et al., 1981; Wilkens, et al., 1982). At 75 μg HEWL/ml. SCN anion appeared more effective than $HCO^-$ but this was not true at 30 μg HEWL/ml. At higher lysozyme concentration, there was greater release of thymidine at the higher salt concentrations tested; however, more lysis was observed at the lower HEWL concentration at lower salt concentrations (compare FIG. 1C to 1A for $HCO_3^-$).

Figure 1D:
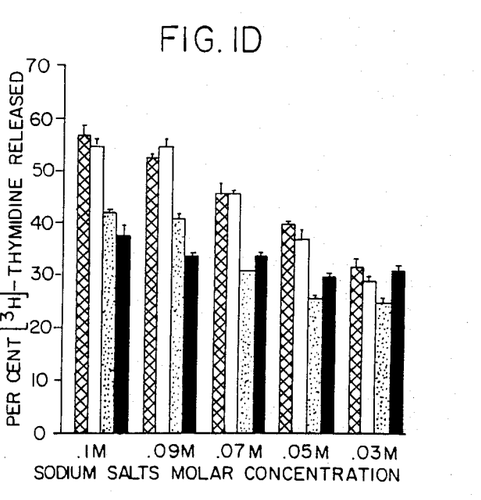

At each HEWL concentration, release of tritiated thymidine was greater in reactions containing both enzymes rather than lysozyme alone. For either the dual enzyme combination of HEWL alone, cell lysis increased as the anion concentration increases, in some cases until plateau levels were reached (see FIG. 1). At 75 μg HEWL/ml, the combination of lysozyme with chymotrypsin was particularly effective as marked changes in the lysis patterns were noted as the salt (particularly $SCN^-$ and $HCO_3^-$) concentration varied. At 30 μg HEWL/ml, there was less lysis at the higher salt concentrations but more lysis at lower salt concentrations compared to 75 μg HEWL/ml (see FIG. 1B and 1D) for the combination enzyme system. At 30 μg HEWL/ml in the presence of chymotrypsin, both chloride and fluoride exhibited lytic potency and were almost as effective as bicarbonate and thiocyanate. Control reaction mixtures or Strep. mutans GS5 treated with chymotrypsin alone were found to release approximately 15 to 20 percent or less of their tritiated thymidine label at all salt concentrations tested.

Lysis by Bicarbonate in low pH Reaction Mixtures

Figure 2:
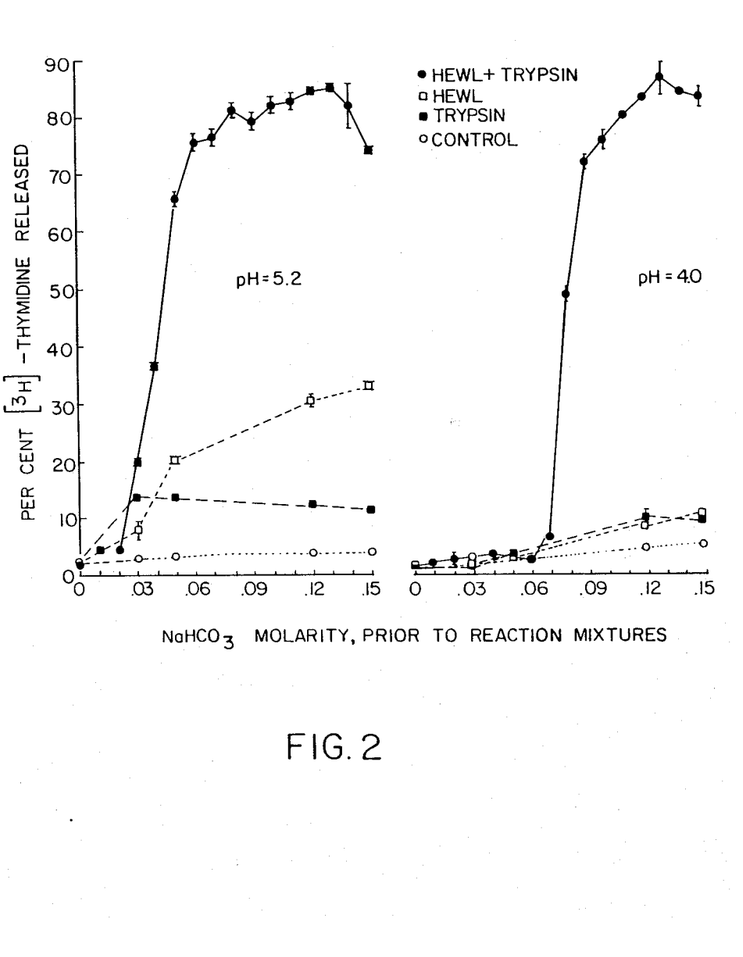
FIGS. 2 and 3 are plates of lysis at different bicarbonate levels and pHs.

In acetate buffer, pH 4.0, lysis is observed only in bicarbonate reaction mixtures containing HEWL and trypsin. (See FIG. 2) In buffer, pH 5.2, HEWL alone caused approximately 30 percent release of radiolabeled thymidine at a final molarity of 0.12M NaHCO3. Comparison of the data indicated that the lysis pattern and the maximum degree of lysis are essentially the same for both pH 4.0 and 5.2 reaction mixtures except that more sodium bicarbonate has to be added at the lower pH in order to initiate the lytic process. From the Henderson-Hasselbach equation, calculations are made to determine the change in concentration of the HCO3 anion upon addition of sodium bicarbonate to low pH reaction mixtures (see Table I).

TABLE I

DETERMINATION OF pH AND CALCULATION OF BICARBONATE CONCENTRATIONS IN LOW pH REACTION MIXTURES

| Buffer | Molarity of Added NaHCO₃ | New pH | New Molarity of HCO₃ |
|---|---|---|---|
| MES pH 5.2 | 0 | 5.2 | 0 |
| | .01 | 5.9 | .004 |
| | .02 | 6.2 | .012 |
| | .03 | 6.5 | .021 |
| | .04 | 6.7 | .031 |
| | .05 | 6.8 | .041 |
| | .06 | 6.9 | .051 |
| | .07 | 7.0 | .062 |
| | .08 | 7.1 | .072 |
| | .09 | 7.2 | .084 |
| | .15 | 7.6 | .140 |
| Acetate, pH 4.0 | 0 | 4.0 | 0 |
| | .01 | 4.2 | .0001 |
| | .05 | 5.0 | .004 |
| | .06 | 5.4 | .009 |
| | .07 | 5.7 | .018 |
| | .08 | 5.8 | .025 |
| | .09 | 6.0 | .038 |
| | .10 | 6.1 | .050 |
| | .11 | 6.2 | .063 |
| | .12 | 6.3 | .073 |
| | .13 | 6.4 | .086 |
| | .15 | 6.5 | .108 |

Figure 3:
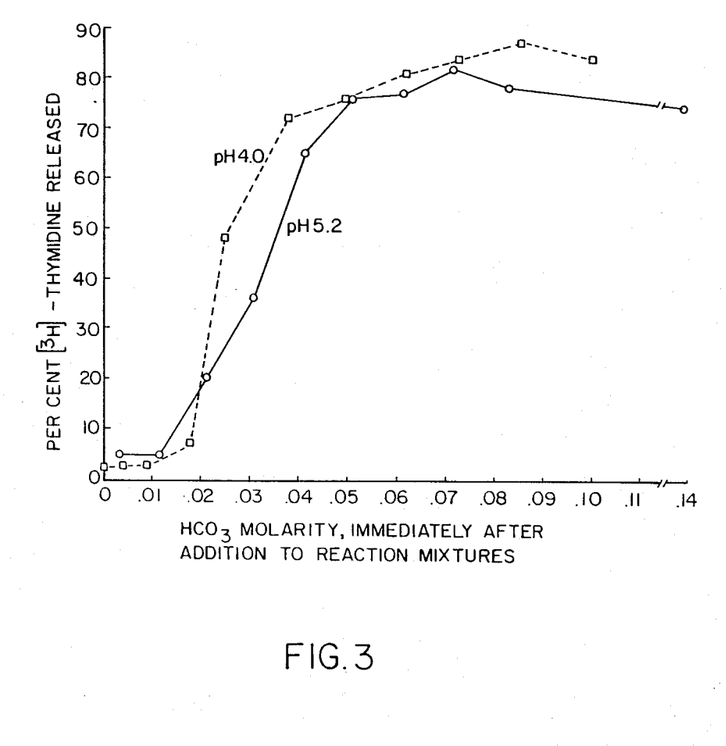

Lysis for pH 4.0 and 5.2 were found to be very similar when curves were generated by plotting release of thymidine versus the $HCO_3$ anion concentrations (see FIG. 3).

Synergism of Fluoride and Bicarbonate Anions

Figure 4:
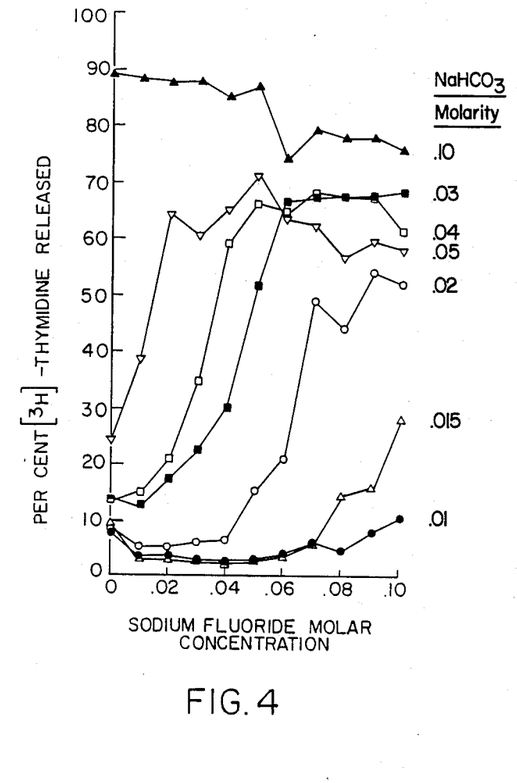
FIG. 4 is a plot of thymidine release from *S. mutans* (lysis) against concentrations of bicarbonate and fluoride.

FIG. 4 illustrates the effect obtained by combining bicarbonate and fluoride in *S. mutans* GS5 lytic studies at pH 5.2. Either in the absence or in the presence of 0.01M NaHCO₃, no significant lytic effect is observed at concentrations of up to 0.08M sodium fluoride. However, at 0.01M NaHCO₃, a concentration which in itself does not yield release of ($^3$H)-thymidine (see FIG. 2), lysis is initiated at concentrations greater than 0.08M NaF. At 0.02M NaHCO₃, lysis is already significant at 0.06M NaF. With increasing concentrations of bicarbonate, lysis increases with still lower fluoride concentrations. However, as the concentration of NaHCO₃ is further raised, the combination with fluoride causes an apparent inhibition of lysis at the higher ionic strengths. At 0.1M NaHCO₃, fluoride does not further enhance the near maximum amount of cell lysis observed. At each sodium bicarbonate concentration, lysis appears to plateau and the higher the bicarbonate concentration, the greater the level of the lytic response.

Lysis by Chloride or Thiocyanate in Combination with Bicarbonate

Figure 5:
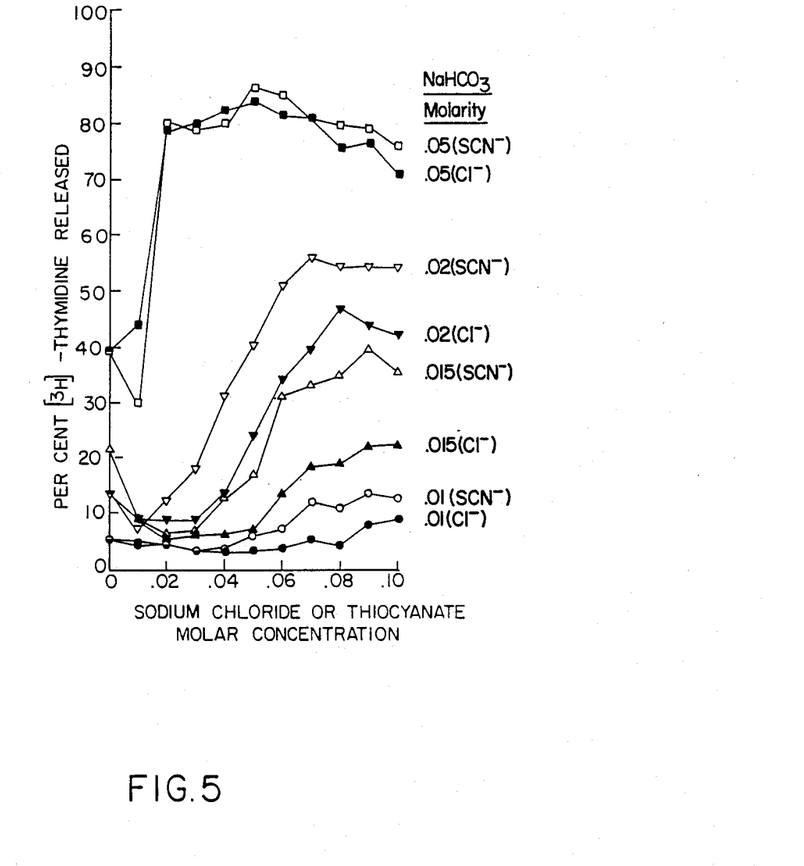
FIG. 5 is a plot of thymidine release from *S. mutans* (lysis) against concentrations of bicarbonate and chloride or thiocyanate.

In combination with fluoride or chloride, bicarbonate appears to show differing lytic effectiveness depending on the concentration of the halide anions (see FIGS. 4 and 5). However, the lytic effect with chlorie or fluoride is not as great as when bicarbonate and thiocyanate are combined and added to the pH 5.2 reaction mixtures (see FIG. 5). At concentrations of 0.01–0.2M sodium chloride or thiocyanate, as explained decrease in tritiated thymidine release is sometimes observed but lysis is found to increase as the anion concentration is further increased. At 0.05M NaHCO₃, there is a steep rise in cell lysis at either 0.02M NaSCN or NaCl (see FIG. 5) similar to that observed for NaF (see FIG. 4).

Lysis with all Four Anions

Figure 6A:
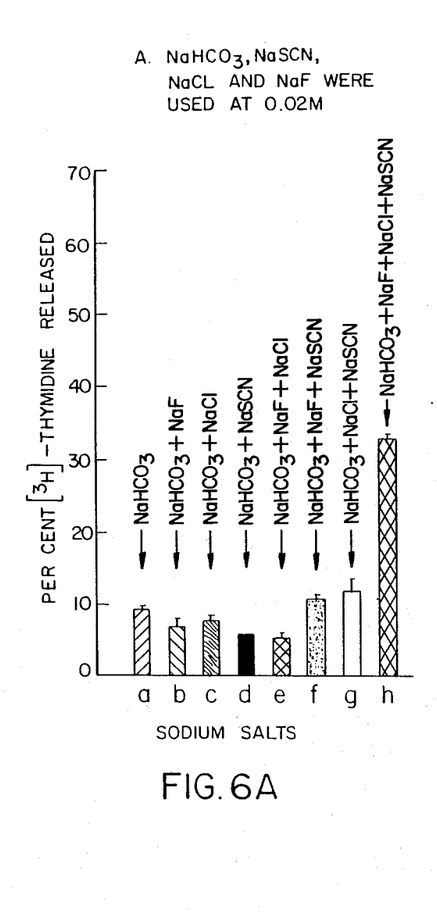
Figure 6B:
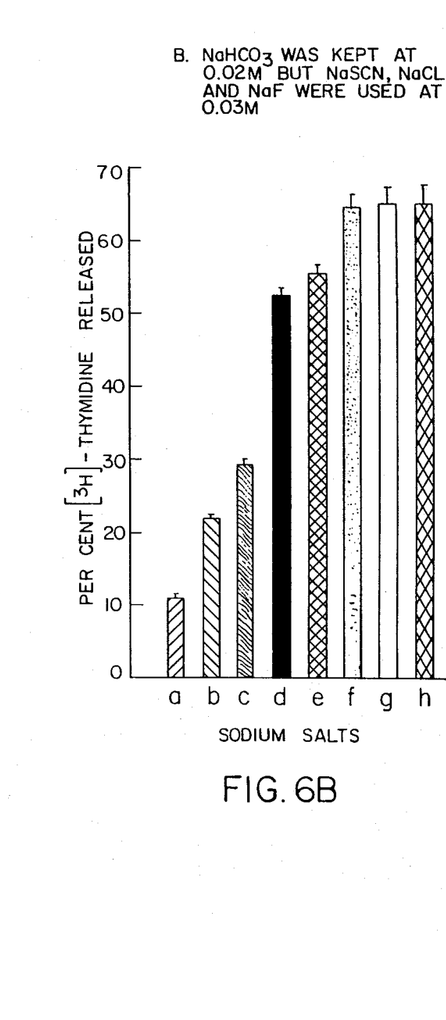
Figure 7A:
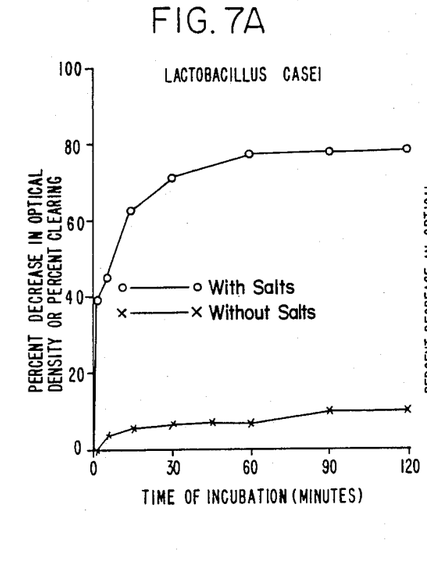
Figure 7B:
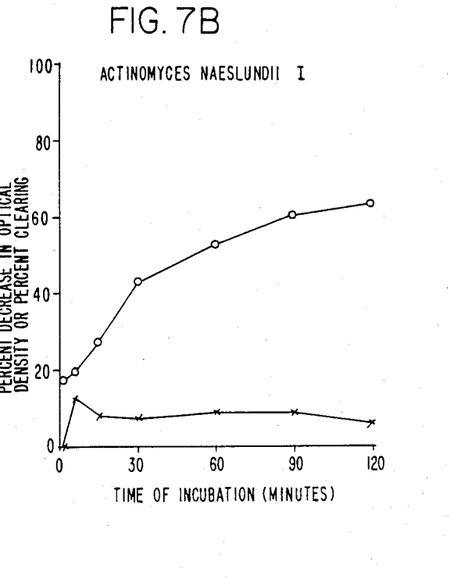
Figure 7C:
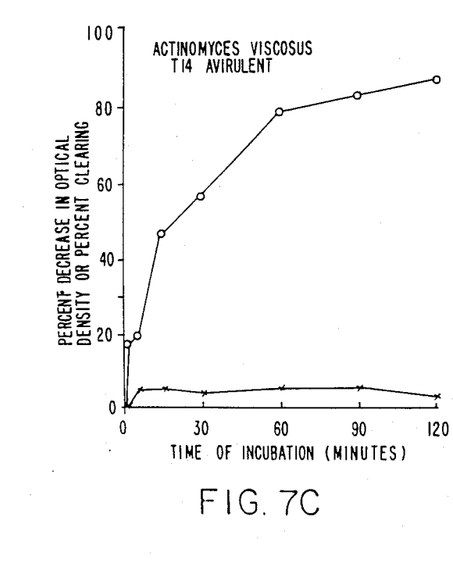
Figure 7D:
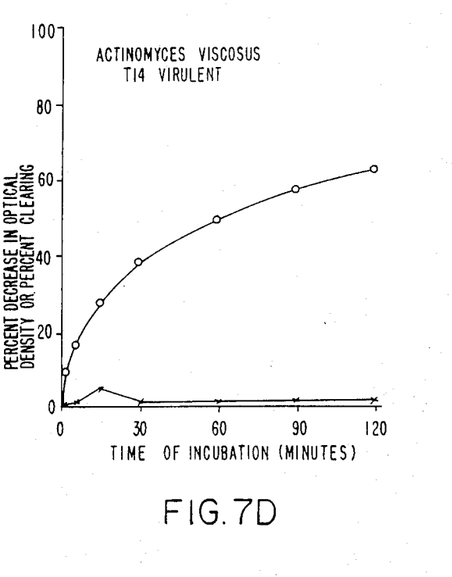

At an apparent sublytic concentration of NaHCO₃, (0.02M), the combination with any two of 0.02M NaF, NaCl and NaSCN does not result in significant release of thymidine from the HEWL-trypsin-treated cells. When NaHCO₃ was combined with all three salts, however, a significant lytic effect is observed (see FIG. 6A). Increasing the concentration of $F^-$, $Cl^-$ and $SCN^-$ to 0.03M while maintaining the $HCO_3^-$ concentration at 0.02M enhances lysis dramatically (see FIG. 6B). Mixtures of bicarbonate and any two of the three sodium results in cell lysis greater than the lysis observed by combining any one of the three salts with bicarbonate, although the combination with NaSCN is almost as effective as a mixture of NaHCO₃, NaCl and NaF.

Lysis Enhancement of Other Oral Cariogenic Bacteria

Bacterical cells are suspended in low ionic strength buffer at low pH (0.025 ionic strength MES buffer, pH 5.2) to simulate the conditions in the mouth at the site of a various lesion; salts were added to yield final concentrations of bicarbonate, thiocyanate and chloride were 0.03M, 0.03M, 0.04M, respectively, and the optical density of the suspension measured at 675 nM. The decrease in turbidity is an indicator of bacterial cell lysis. (FIG. 7, Table II).

TABLE II

DECREASE IN TURBIDITY OF ORAL MICROORGANISMS UPON ACTIVATION OF LYSOZYME-TRYPSIN-DAMAGED BACTERIA BY SODIUM BICARBONATE, SODIUM THIOCYANATE AND SODIUM CHLORIDE.

Optical Density (Absorption) at 675 nm[a]

| Incubation Time (Minutes)[b] | *Lactobacillus casei* Lysozyme + Trypsin | *Lactobacillus casei* Lysozyme + Trypsin + Salts[c] | *Actinomyces naeslundii* I Lysozyme + Trypsin | *Actinomyces naeslundii* I Lysozme + Trypsin + Salts | *Actinomyces viscosus* Avirulent Lysozyme + Trypsin | *Actinomyces viscosus* Avirulent Lysozyme + Trypsin + Salts | *Actinomyces viscosus* T 14 Virulent Lysozyme + Trypsin | *Actinomyces viscosus* T 14 Virulent Lysozyme + Trypsin + Salts |
|---|---|---|---|---|---|---|---|---|
| 0 | .335 | .310 | .222 | .208 | .299 | .296 | .227 | .244 |
| 0.5 | .335 | .188 | .222 | .171 | .299 | .243 | .227 | .222 |
| 5 | .322 | .160 | .190 | .168 | .283 | .231 | .225 | .204 |
| 15 | .318 | .101 | .204 | .142 | .279 | .151 | .216 | .176 |
| 30 | .314 | .071 | .206 | .118 | .283 | .107 | .228 | .149 |
| 60 | .310 | .052 | .201 | .099 | .281 | .064 | .238 | .123 |
| 90 | .300 | .050 | .201 | .083 | .279 | .052 | .244 | .103 |
| 120 | .299 | .047 | .207 | .073 | .289 | .039 | .237 | .092 |

In Vivo Elimination and Reduction of S. mutans from the Plaque of Hamsters by treatment with Sodium Salts of Bicarbonate, Thiocyanate and Chloride The purpose of this evaluation was to determine if *S. mutans* colonization of the tooth surfaces of the hamster could be inhibited or reduced by the administration of solutions containing either 0.03M sodium bicarbonate or 0.03M sodium bicarbonate in combination with 0.03M sodium chloride and 0.03M sodium thiocyanate. The molar teeth of Golden Syrian Hamsters were infected with *S. mutans* 6715-15, a highly cariogenic strain, by brushing and by inoculation of the bacteria into the drinking water. After 30 days of colonization, a four-week experiment was initiated in which control animals (no salts) were compared to those treated with either sodium bicarbonate or with all three sodium salts. No effect was observed on *S. mutans* colonization in either the control group or in the treatment group with sodium bicarbonate alone. However, at the end of four weeks if sodium bicarbonate was used in combination with sodium chloride and sodium thiocyanate, 50% of the animals had no *S. mutans* in their plaque while the remaining 50% had only minimal numbers of the organism. Moreover, already by the end of the third week, a significant reduction of *S. mautans* was noted in the plaque of those animals being treated with the combination of the three salts. (Pollock, et al., Infect. Immun., 45, pp. 610-617 (1984)).

PROTOCOL

Evaluation of the Cariostatic

Activity in the Hamster Caries Model

METHODS

Animals

Twenty-one day old Golden Syrian hamsters were utilized and were divided into groups of 10 animals per group for the evaluation of the test materials.

ANIMAL INOCULATION

Organism

The organism used for oral inoculation of the test animals were *S. mutans* 6715-15. This organism was originally obtained from the American Type Culture Collection (ATCC 27352). This organism has been routinely used to inoculate stock animals at Stony Brook and the organism has been reisolated from the stock animal and the isolate was identified as *S. mutans* by biochemical reactions. Passage in hamsters has been carried out to maintain the cariogenic potential of the organism.

Identification of the Organism

The organism was identified as *S. mutans* by its formation of acid from sorbitol, mannitol and inulin; and its inability to release ammonia from arginine; by its resistance to 20 mg% streptomycin and inability to grow in 6.5% sodium chloride. Stock cultures of the organism were made and these stock cultures were freeze-dried for use in the oral inoculation of the test animals.

Inoculation Procedure

The animals were received as 21-day old animals and weighing 21 to 22 grams. On the 24th day of age, the study was initiated. Inoculation of each of the animals was carried out for a seven-day period by the daly oral inoculation of an 18 to 24 hour Brain Heart Infusion broth culture of the test organism. Approximately 0.2 ml of the broth culture was brushed onto the molar teeth of each animal using a #8 camel's hair brush. The animals were induced to bite on the brush using their molar teeth to assist in retention of the organism in the plaque. In addition to this, 10 ml of the broth culture was added to each 100 ml of drinking water each day.

Plaque Samples

Plaque samples were taken approximately 10 days after completion of the oral inoculation of each of the animals. This procedure was carried out to assure that the inoculation of *S. mutans* had been successful and that the animals had in fact retained the organism in their plaque. One or two animals were randomly selected from each cage. Plaque samples were removed from the molar teeth and these plaque samples were examined from *S. mutans*. The results obtained did indicate that all of the animals so tested harbored *S. mutans*. On the 10th day, the animals were randomized and treatment was initiated.

Caging

The animals were grouped five animals to a cage in plastic cages and each cage was supplied with wood shavings and each cage was provided with Diet 2000 (56% sucrose) and water ad libitum.

Treatment

All treatments were carried out by putting the test materials into the drinking water and providing fresh solutions of various test materials three times a week. Groups involved in this evaluation were water controlled groups, a sodium fluoride group with a fluoride concentration of 20.0 ppm, a sodium chloride-sodium thiocyanate group in which each salt was 60 millimolar, a sodium bicarbonate group which received 30 millimolar bicarbonate, a bicarbonate-thiocycnate combination in which the bicarbonate concentration was 30 millimolar and the thiocyanate concentration was 60 millimolar, a bicarbonate-chloride combination in which the bicarbonate concentration was 30 millimolar and chloride concentration was 60 millimolar and a bicarbonate-thiocyanate-chloride group in which the bicarbonate concentration was 30 millimolar, the thiocyanate was 60 millimolar, and the chloride was 60 millimolar.

The treatment was carried out over a 90-day period. Treatment was ad libitum. At the end of the 90-day treatment period the animals was sacrificed, decapitated and the jaws defleshed and scored for caries according to the methods of Keyes. The results of this evaluation are given in the accompanying Table.

Results

The results in Table 3 show that even under these extreme three-month sugar feeding conditions in the hamster, bicarbonate in combination with either chloride or in combination with thiocyanate plus chloride was extremely effective in reducing the extent of dental caries. In comparison to fluoride alone, there was a more than doubling of the anti-caries activity by bicarbonate and chloride. Although bicarbonate alone was also effective, the data was only statistically significant by the Student t-test and not by the more rigorous Analysis of Variance. Since one employs extreme sugar feeding conditions in animal-caries model systems, a positive result indicates a high probability of success in human studies. It should be pointed out that even greater caries reductions would be expected by slight increases in the concentrations of bicarbonate in combination with the other anions.

TABLE 3

Summary of the Evaluation of the Anti-Cariostatic Activity Using the Combination of Selected Anions in the Hamster-Caries Model System.

| GROUP | Concentration/Anion (mM) | | | Average Score/ Animal | Caries Reduction Percent |
|---|---|---|---|---|---|
| | $HCO_3^-$ | $SCN^-$ | $Cl^-$ | | |
| Water Control | — | — | — | 33.5 | — |
| NaF | (20 ppm $F^-$) | | | 24.6 | 27* |
| $Cl^- + SCN^-$ | — | 60 | 60 | 24.3 | 27* |
| $HCO_3^-$ | 30 | — | — | 17.8 | 47+ |
| $HCO_3^- + SCN^-$ | 30 | 60 | — | 20.1 | 40+ |
| $HCO_3^- + Cl^-$ | 30 | — | 60 | 14.2 | 58++ |
| $HCO_3^- + SCN^- + Cl^-$ | 30 | 60 | 60 | 15.3 | 54++ |

*Positive trend in comparison to controls, but not statistically significant.
+Statistically significant by the Student t-test, $p \leq .025$.
++Statistically significant by the Analysis of Variance, $p \leq .05$.

Lysis of Fusobacterium Nucleatum at neutral pH

Figure 8:
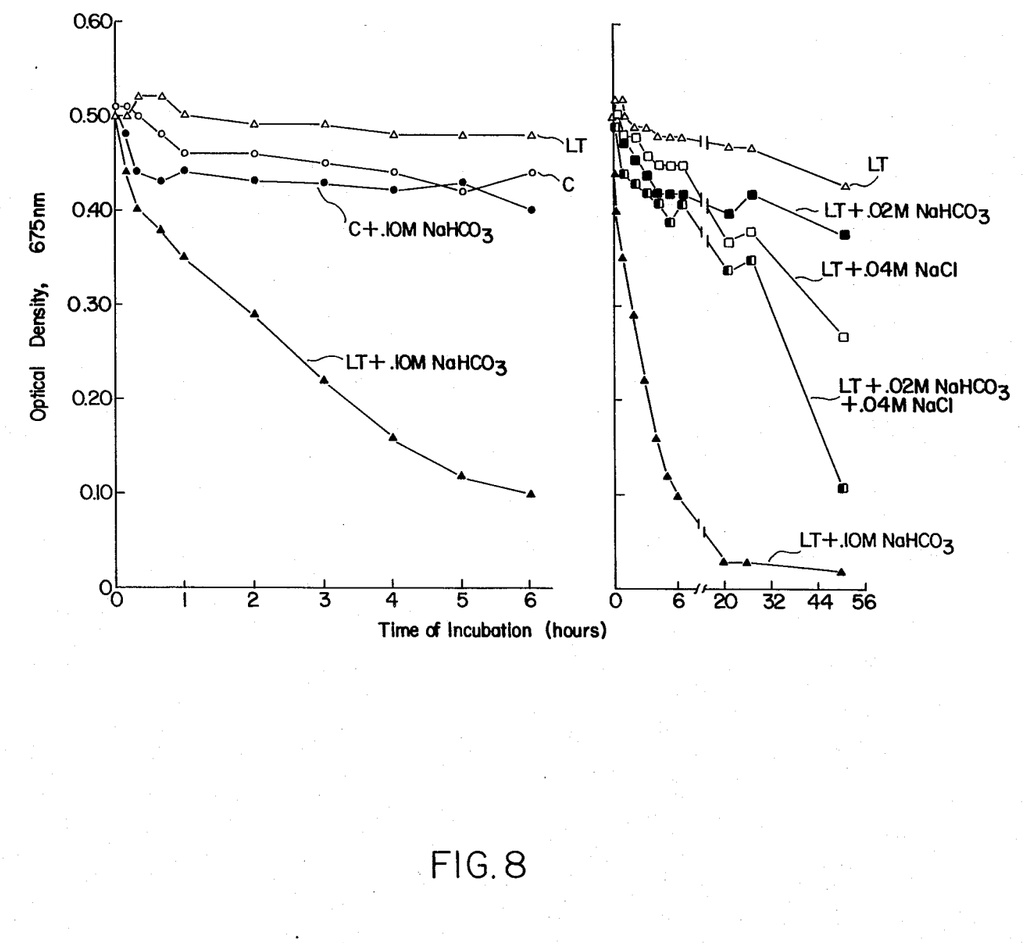
FIG. 8 is a plot of the thymidine release from *F. nucleatum* comparing the lysis of lysozyme/trypsin treated cells or control cells using bicarbonate, chloride or combinations of these anions as lytic activators.
Figure 9:
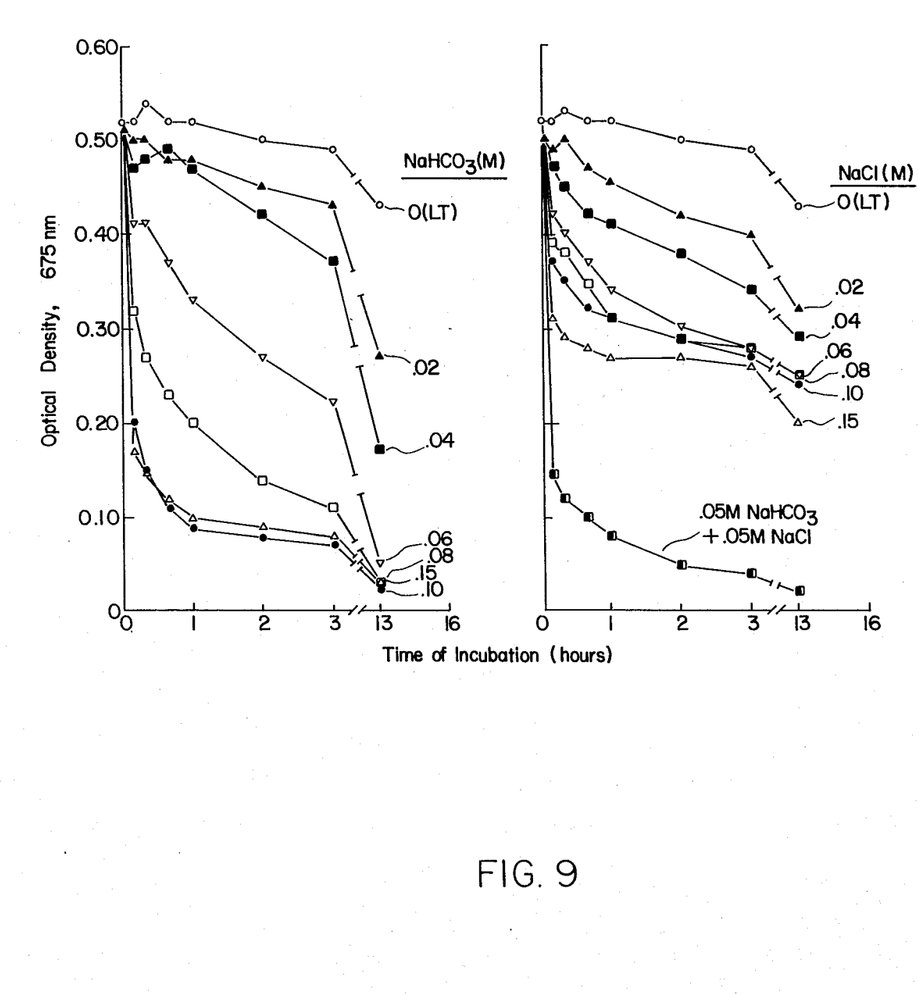
FIG. 9 is a plot of thymidine release from *F. nucleatum* comparing the lusis of lysozyme/trypsin treated cells at a variety of bicarbonate and chloride concentrations.

The results of FIGS. 8 and 9 show that even at neutral pH, the effects of the salt combination of bicarbonate and chloride are synergistic for the lysis of *F. nucleatum*. In FIG. 8 (left side) note that both the lysozyme-trypsin cells and the control cells (no additives) are fairly stable and lose little turbidity over time. However, treatment of the lysozyme-trypsin (LT) cells with 0.10M $NaHCO_3$ (final concentration) leads to lysis (as measured by the decrease in turbidity or clearing of the bacterial cell suspension). Still in FIG. 8 (right side), note that even after 50 h, the lysozyme-trypsin cells lose little turbidity but that cells treated with 0.01M $NaHCO_3$ (sodium bicarbonate) continue to lyse further. In the LT cells treated with the combination of 0.02M $NaHCO_3$ and 0.04M NaCl (sodium chloride), lysis is significantly greater than LT cells treated with either 0.02M $NaHCO_3$ or 0.04M NaCl alone.

In FIG. 9, all the cells have been treated with lysozyme and trypsin. Lysis is dependent on the final concentration of sodium bicarbonate or sodium chloride. Note that sodium bicarbonate is more effective than sodium chloride, particularly, as concentrations increase beyond 0.04M. In the right graph (and pertinent to the invention), note the rapid rate of lysis when 0.05M $NaHCO_3$ is used in combination with 0.05M NaCl. The lysis rate of this combination is far greater than would be expected from adding the rates of lysis for 0.05M $NaHCO_3$ and 0.05M NaCl when either are used alone. The cells in FIG. 9 were grown to a slightly lower optical density than those of FIG. 8. Also in FIG. 9, both a higher lysozyme and a higher trypsin concentration were used which may account for the more rapid lysis of the cells (compare treatment of LT cells with 0.10M $NaHCO_3$ in FIGS. 8 and 9—the rate is faster in FIG. 9).

The following Examples describe in detail formulations encompassing the compositions of the present invention. It will be apparent to those skilled in the art that many modifications, both of materials and methods, may be practiced without departing from the spirit and scope of the invention.

EXAMPLE I

| Mouth Spray | |
|---|---|
| Peppermint Spirit | 43.2 ml. |
| Saccharin Sodium | 0.07 gm. |
| Sodium bicarbonate | 0.25–3.24 gm. |
| Water to | 300.0 ml. |
| Can Also Add: | |
| Sodium Fluoride (if desired) | 0.25–1.26 gm |
| Sodium Chloride and/or | 0.23–1.76 |
| Sodium thiocyanate | 0.49–2.4 gm |

The formulation is utilized by spraying aliquots of 0.25 to 0.50 ml onto each quadrant of the gingiva and tooth surface between 1 and 3 times per day.

EXAMPLE II

| Mouthwash Formulation | |
|---|---|
| Sodium Bicarbonate | 0.84–10.8 gm. |
| Thymol | 0.5 gm. |
| Eucalyptol | 1.0 ml. |
| Methyl salicylate | 0.5 ml. |
| Amaranth solution | 14.0 ml. |
| Alcohol | 50.0 ml. |
| Glycerin | 100.0 ml. |
| Water to | 1000.0 ml. |
| Can Also Add: | |
| Sodium fluoride (if desired) | 0.084–4.20 gm. |
| Sodium chloride and/or | 1.17–5.85 gm. |
| Sodium thiocyanate | 1.62–8.0 gm. |

The formulation is utilized by rinsing the mouth for about 30–60 seconds from 1–3 times per day with 10 to 15 ml of undiluted wash.

EXAMPLE III

| Toothpaste Gel Formulation | |
|---|---|
| Carboxymethyl cellulose 120H | 1.8 gm. |
| Glycerin | 2.0 ml. |
| Propylene glycol | 39.0 ml. |
| Purified water | 27.0 ml. |
| Methyl paraben | 0.2 gm. |
| Saccharin sodium (50% sol.) | 0.2 ml. |
| Peppermint Oil | 0.6 ml. |
| Mineral Oil | 2.0 ml. |
| Triton X-100 | 5.0 gm. |
| Silica | 21.0 gm. |
| Sodium bicarbonate | 0.08–1.08 gm. |
| Can Also Add: | |
| Sodium fluoride (if desired) | 0.084–0.42 gm. |
| Sodium chloride and/or | 0.12–0.59 gm. |

| -continued | |
|---|---|
| Sodium thiocyanate | 0.16–0.80 gm. |

The formulation is utilized by cleaning the teeth with about 1 to 2 gm. of the paste between 1 and 3 times per day.

EXAMPLE IV

| | Each Stick |
|---|---|
| Chewing Gum | |
| Gum Base: | |
| Estergum | 142 mg. |
| Coumarone Resin | 213 mg. |
| Latex (dry) | 71 mg. |
| Paraffin Wax (melting pt. 180° F.) | 47 mg. |
| Sorbitol (for sugarless gum) | 1309 mg. |
| Corn Syrup (Baume 45° C.) | 400 mg. |
| Flavoring | q.s. |
| Sodium Bicarbonate | 0.2–43 mg. |
| Can Also Add: | |
| Sodium Fluoride (if desired) | 0.2–16 mg. |
| Sodium Chloride and/or | 0.3–23 mg. |
| Sodium Thiocyanate | 0.4–32 mg. |

The formulation is utilized as needed.

EXAMPLE V

| | Each Tablet |
|---|---|
| Breath Freshener Tablet | |
| Wintergreen Oil | 0.6 mg. |
| Talc | 10.0 mg. |
| Menthol | 0.85 mg. |
| Peppermint Oil | 0.3 mg. |
| Sodium Saccharin | 0.3 mg. |
| Mannitol USP (powdered) | 180.95 mg. |
| Sodium Stearate | 2.0 mg. |
| Sodium Bicarbonate | 0.2–43 mg. |
| Sorbitol USP (powdered) | 180.0 mg. |
| Lactose USP (powdered) (q.s.) | 1.0 gm. |
| Can Also Add: | |
| Sodium Fluoride (if desired) | 0.2–16 mg. |
| Sodium Chloride and/or | 0.3–23 mg. |
| Sodium Thiocyanate | 0.4–32 mg. |

The formulation is utilized as needed.

EXAMPLE VI

| | Each Tablet |
|---|---|
| Chewable Multivitamin Tablet | |
| Vitamin A USP (dry stabilized form) | 5000 USP units |
| Vitamin D (dry stabilized form) | 400 USP units |
| Ascorbic Acid USP | 60 mg. |
| Thiamine HCl USP | 1 mg. |
| Riboflavin HCl | 1.5 mg. |
| Pyridoxine HCl USP | 1 mg. |
| Cyanocobalamin USP | 2 ug. |
| Calcium Pantothenate USP | 3 mg. |
| Niacinamide USP (granular) | 10.0 mg. |
| Mannitol USP (granular) | 236.2 mg |
| Corn Starch | 16.6 mg. |
| Sodium Saccharin | 1.1 mg. |
| Sodium Stearate | 6.6 mg. |
| Talc | 10.0 mg. |
| Wintergreen Oil | 1.2 mg. |
| Menthol | 1.7 mg. |
| Peppermint Oil | 0.6 mg |
| Sodium Bicarbonate | 0.2–43 mg. |
| Can Also Add: | |
| Sodium Fluoride (if desired) | 0.2–16 mg. |

| -continued | |
|---|---|
| | Each Tablet |
| Sodium Chloride and/or | 0.3–23 mg. |
| Sodium Thiocyanate (if desired) | 0.4–32 mg. |

The formulation is utilized by taking and chewing one tablet each day.

EXAMPLE VII

| | Each Tablet |
|---|---|
| Candy (Lozenge) | |
| Acacia | as required for binding |
| Mannitol (powdered) USO | 180.0 mg. |
| Sodium Saccharin | 1.1 mg. |
| Sodium Stearate | 5.0 mg. |
| Licorice | 98.0 mg. |
| Talc | 10.0 mg. |
| Capsicum | 2.0 mg. |
| Menthol | 1.8 mg. |
| Lactose (powdered) USP (q.s.) | 2.0 gm. |
| Sodium Bicarbonate | 0.2–43 mg. |
| Can Also Add: | |
| Sodium Fluoride (if desired) | 0.2–16 mg. |
| Sodium Chloride and/or | 0.3–23 mg. |
| Sodium Thiocyanate (if desired) | 0.4–32 mg. |

The formulation is utilized as needed.

EXAMPLE VIII

| | |
|---|---|
| Toothpaste Formulation | |
| Carboxymethyl cellulose 120H | 1.8 gm. |
| Glycerin | 2.0 ml. |
| Propylene glycol | 39.0 ml. |
| Purified water | 27.0 ml. |
| Methyl paraben | 0.2 gm. |
| Saccharin sodium (50% sol.) | 0.2 ml. |
| Peppermint Oil | 0.6 ml. |
| Mineral Oil | 2.0 ml. |
| Triton X-100 | 5.0 gm. |
| Dicalcium Phosphate | 21.0 gm. |
| Sodium bicarbonate | 0.08–1.08 gm. |
| Can Also Add: | |
| Sodium fluoride (if desired) | 0.084–0.42 gm. |
| Sodium chloride and/or | 0.12–0.59 gm. |
| Sodium thiocyanate | 0.16–0.80 gm. |

The formulation is utilized by cleaning the teeth with about 1 to 2 gm. of the paste between 1 and 3 times per day.

We claim:

1. A method of enhancing the lysis of cariogenic bacteria, periodontopathic bacteria or plaque-forming bacteria, which comprises administering to the teeth of a mammal in need of therapy against such bacteria an effective amount of a composition comprising from about 0.08% to about 1.6% bicarbonate anion, and from about 0.08% to about 1.8% of a monovalent anion selected from the group consisting of chloride, thiocyanate and fluoride or mixtures thereof in a vehicle suitable for oral or oral cavity administration, said composition being essentially free of bivalent anion.

2. A method according to claim 1 wherein the composition is administered as a chewable composition selected from the group consisting of chewing gum, a vitamin supplement or a candy.

3. A method according to claim 1 wherein the composition is administered as a composition selected from the group consisting of toothpaste, gel, mouthwash or mouth spray.

* * * * *